US012303628B2

(12) United States Patent
Silvast-Äikäs et al.

(10) Patent No.: US 12,303,628 B2
(45) Date of Patent: May 20, 2025

(54) MEASUREMENT AND AUTOMATED PERITONEAL DIALYSIS APPARATUS AND METHOD THEREFOR

(71) Applicant: SMART PD SOLUTIONS OY, Helsinki (FI)

(72) Inventors: Pirgit Silvast-Äikäs, Helsinki (FI); Markku Känsäkoski, Helsinki (FI)

(73) Assignee: SMART PD SOLUTIONS OY, Helsinki (FI)

( * ) Notice: Subject to any disclaimer, the term of this patent is extended or adjusted under 35 U.S.C. 154(b) by 458 days.

(21) Appl. No.: 17/920,584

(22) PCT Filed: Apr. 20, 2021

(86) PCT No.: PCT/EP2021/060145
§ 371 (c)(1),
(2) Date: Oct. 21, 2022

(87) PCT Pub. No.: WO2021/214006
PCT Pub. Date: Oct. 28, 2021

(65) Prior Publication Data
US 2023/0173153 A1 Jun. 8, 2023

(30) Foreign Application Priority Data
Apr. 22, 2020 (FI) .................................... 20205404

(51) Int. Cl.
*A61M 1/28* (2006.01)
*A61M 1/16* (2006.01)
*B01D 61/24* (2006.01)

(52) U.S. Cl.
CPC ............ *A61M 1/28* (2013.01); *A61M 1/1605* (2014.02); *A61M 1/1609* (2014.02); *B01D 61/24* (2013.01);
(Continued)

(58) Field of Classification Search
CPC .... A61M 1/1605; A61M 1/1609; A61M 1/28; A61M 2205/3317; A61M 2205/3327;
(Continued)

(56) References Cited

U.S. PATENT DOCUMENTS

| 5,670,057 A | 9/1997 | Chen et al. |
| 2003/0216677 A1 | 11/2003 | Pan et al. |

(Continued)

FOREIGN PATENT DOCUMENTS

| WO | 2019/118929 | 6/2019 |
| WO | 2019/1189292 | 6/2019 |

OTHER PUBLICATIONS

International Search Report for PCT/EP2021/060145, mailed Jul. 5, 2021, 10 pages.
(Continued)

*Primary Examiner* — John Kim
(74) *Attorney, Agent, or Firm* — Nixon & Vanderhye PC

(57) ABSTRACT

A measurement apparatus for a peritoneal dialysis apparatus (10) comprises a connecting means (102), which is in contact with a drain line system (104) of the peritoneal dialysis apparatus (10), and electrochemical sensor means (110). The measurement apparatus (100) receives spent dialysate through the drain line system (104) when the dialysis apparatus (10) is connected with a patient (12). The electrochemical sensor means (110), which is in contact with the spent dialysate, outputs an electric signal in response to contents of urea and glucose of the spent dialysate for data processing and/or data presentation of the electric signal.

11 Claims, 3 Drawing Sheets

(52) U.S. Cl.
CPC ............... *A61M 2205/3317* (2013.01); *A61M 2205/3327* (2013.01); *A61M 2205/3334* (2013.01); *A61M 2205/502* (2013.01); *A61M 2205/702* (2013.01); *A61M 2205/75* (2013.01)

(58) Field of Classification Search
CPC .... A61M 2205/3334; A61M 2205/502; A61M 2205/702; A61M 2205/75; B01D 61/24
See application file for complete search history.

(56) References Cited

U.S. PATENT DOCUMENTS

| | | |
|---|---|---|
| 2009/0036825 A1 | 2/2009 | Petersen |
| 2012/0029325 A1 | 2/2012 | Neftel |
| 2014/0190886 A1 | 7/2014 | Pudil et al. |
| 2018/0043080 A1 | 2/2018 | Gerber et al. |
| 2018/0221555 A1 | 8/2018 | Rohde et al. |
| 2018/0256085 A1 | 9/2018 | Farooqui et al. |
| 2019/0358387 A1 | 11/2019 | Elbadry et al. |
| 2019/0381231 A1 | 12/2019 | Tsoory et al. |

OTHER PUBLICATIONS

Search Report for FI20205404 dated Nov. 5, 2020, 2 pages.
Written Opinion of the International Preliminary Examining Authority, mailed Apr. 26, 2022, 7 pages.

MEASUREMENT AND AUTOMATED PERITONEAL DIALYSIS APPARATUS AND METHOD THEREFOR

This application is the U.S. national phase of International Application No. PCT/EP2021/060145 filed Apr. 20, 2021, which designated the U.S. and claims priority to FI 20205404 filed Apr. 22, 2020, the entire contents of each of which are hereby incorporated by reference.

FIELD

The invention relates to a measurement apparatus for a peritoneal dialysis apparatus, an automated peritoneal dialysis apparatus and a measuring method of a peritoneal dialysis apparatus.

BACKGROUND

Patients with a full or partial loss of kidney function may be treated using a renal replacement therapy such as hemodialysis and peritoneal dialysis. The hemodialysis is performed in a hospital whereas the peritoneal dialysis can be carried out at home by the patient. In automated peritoneal dialysis, the peritoneum that is in the abdominal cavity is used to remove wastes and water from the blood. Although it is known that the automated peritoneal dialysis is rather efficient, the present knowledge is inadequate to determine how well peritoneal dialysis really works.

Hence, an improvement of the peritoneal dialysis would be welcome.

BRIEF DESCRIPTION

The present invention seeks to provide an improvement in the measurements.

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example an automated peritoneal dialysis apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

At present, a problem of the peritoneal dialysis is that the effectiveness of the treatment of peritoneal dialysis, such as how the peritoneum works, can only be measured by a manual work in which the patient provides 4 bags per day as samples from the drainage bags. The patient has to keep record of when the drainings and administrations started, how much the bags weighed, what kind of solutions he/she used. The patient brings the collected samples and records to a hospital, and a nurse processes the samples and submits them for further analysis. The nurse has to copy the results obtained to a hospital's computer, which then computes the patient's peritoneum properties. The nurse also simulates various machine therapy models based on the results obtained. The method is extremely laborious, error prone, and complicated for the patient, especially if he or she has performed, as a rule, night-time treatment with the dialysis apparatus. This all takes nowadays about two working days and the patient may receive the result as late as one to two months after he/she did his/her part.

Figure 1:
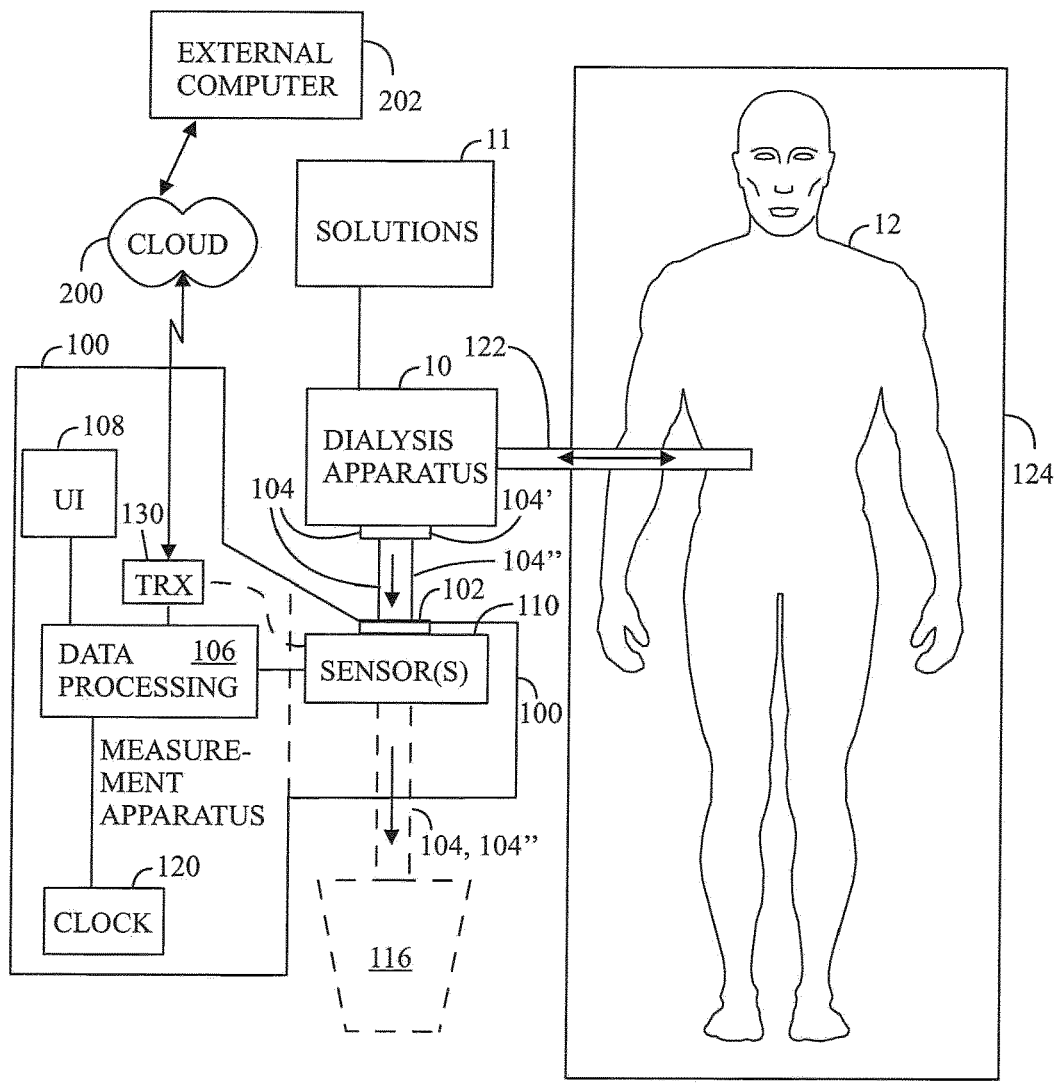

FIG. 1 illustrates an example of an automated peritoneal dialysis apparatus 10, which comprises a measurement apparatus 100. The automated peritoneal dialysis apparatus 10 also comprises or is connected with a bank 11 of peritoneal solutions, the bank 11 containing at least one solution. However, the measurement apparatus 100 is not necessarily a part of the automated peritoneal dialysis apparatus 10 but it may be a separate device connectable to the automated peritoneal dialysis apparatus 10.

A peritoneal dialysis may be performed during night when a patient 12 is sleeping in a bed 124 at his/her home, for example. The measurement apparatus may be disposable. The measurement apparatus 100 for the peritoneal dialysis apparatus 10 comprises a connector 102, which can be connected with a drain line system 104 of the peritoneal dialysis apparatus 10 at least when the peritoneal dialysis apparatus 10 is used for the peritoneal dialysis. The connector 102 may a tube connector. The tube connector may have thread, its attachment may be based on suitable shape in order to have a tight connection, and/or on friction. The measurement apparatus 100 also comprises at least one electrochemical sensor 110, which comprises a tube with at least one electrochemical sensor element. Additionally, the measurement apparatus 100 comprises or is connected with a data processing unit 106 and a user interface 108.

A person skilled in the art is familiar with an operation of the at least one electrochemical sensor 110, per se. The operation of the at least one electrochemical sensor 110 may be based on enzymatic catalysis, for example. The at least one electrochemical sensor 110 and its connector 102 are dispensable, that is, they are used for only one dialysis. The at least one electrochemical sensor 110 is continuously operating for a few hours, and may be based on potentiometric detection.

At least one electrochemical biosensor measures urea concentration of spent dialysate. Measurement technology of urea biosensor may be based on 1) enzymatic hydrolysis of urea ($CH_4N_2O$) molecule by immobilized urease enzyme activated by enzyme activation solution, and/or 2) ion selective electrochemical measurement of generated ammonium ($NH4+$) ion based on potentiometric detection. To improve $NH4+$ ion selective properties of biosensor, the sensor may be treated with ammonium ionophore.

To avoid $Na+$ ion disturbances to $NH4+$ detection differential electrochemical measurement is employed: Corrections for background in electrochemistry is done by measuring potential differences between two points (with and without urease enzyme).

The measurement apparatus 100 receives spent dialysate through the drain line system 104 of the peritoneal dialysis apparatus 10 when the dialysis apparatus 10 is connected with the patient 12 using a patient tube 122.

The at least one electrochemical sensor 110, which is in contact with a flow of the spent dialysate, continuously outputs at least one electric signal in response to contents of urea and glucose of the spent dialysate. Parameters of the signal carry information on the contents of urea and glucose.

In an embodiment, the at least one electrochemical sensor 110 may be based on a porous silk fibroin membrane with immobilized urease mounted in a housing of polydimethylsiloxane. In an embodiment, the at least one electrochemical sensor 110 may be based on electropolymerization of 3,4-ethylenedioxythiophene monomer on a hierarchical network of carbon nanotubes and gold nanotubes. In an embodiment, the at least one electrochemical sensor 110 may be based on metalloenzymes (urease or uricase), the metalloenzymes being synthetic or natural. In an embodiment, the at least one electrochemical sensor 110 may be based on enzymes free electrochemical detection.

In an embodiment, the at least one electrochemical sensor 110 may detect glucose based on amperometric-sensing where glucose is oxidized, which leads to generation of hydrogen peroxide and the hydrogen peroxide is finally detected by electrodes of the at least one electrochemical sensor 110. These are only examples of possibilities of the at least one electrochemical sensor 110 without limiting to these. A person skilled in the art is familiar with electrochemical sensors, per se.

The data processing unit 106 correspondingly processes the at least one electric signal and form a percentage of urea and a percentage of glucose of the spent dialysate based on the at least one electric signal in a continuous manner.

Any detector such the at least one electrochemical sensor 110 integrates over a certain period its input in order to form its output. Despite such a feature the measurement may be considered continuous. Additionally, even when the measurement apparatus 100 is digital and it outputs discrete values one after another, the measurement is considered continuous.

In an embodiment, the user interface 108 may then present the percentage of urea and the percentage of glucose. In an embodiment, the user interface 108 comprises a screen, a keyboard and/or a touchscreen. In an embodiment, the user interface 108 may comprise a loudspeaker. In an embodiment, the user interface 108 may present the percentage of urea and the percentage of glucose in a continuous manner. In an embodiment, the user interface 108 may present the percentage of urea and the percentage of glucose in a continuous manner after a delay. The delay may be as long as a duration of the dialysis. In this manner, the percentage of urea and the percentage of glucose may be presented in the morning if the peritoneal dialysis was performed at night prior to the morning. The measurement apparatus 100 may thus comprise the connector 102 and the at least one electrochemical sensor 110 (see the vertical dashed line between the data processing unit 106 and the sensor(s) 110 in FIG. 1), or the measurement apparatus 100 may comprise the connector 102, the at least one electrochemical sensor 110 and the data processing unit 106. The data processing unit 106 may further comprise or connected with the user interface 108. In various embodiments, the measurement apparatus 100 may comprise additional components and/or devices.

Note that the data processing unit 106 may, in an embodiment, be directly connected with the measurement apparatus 100, or the measurement apparatus 100 may comprise a transmitter 130, which is directly connected with the at least one electrochemical sensor 110 (see curved and dashed line therebetween), and the measurement apparatus 100 is connected through the transmitter 130 with an external computer 202, which may comprise the data processing unit 106 for processing the data.

In an embodiment, the measurement apparatus 100 may comprise a flow meter 112, which may feed data on the flow of the spent dialysate (measuring the total volume of spent dialysate drained out) that is received by the measurement apparatus 100 to the data processing unit 106 during a drain-phase. The data processing unit 106 may detect an order of different flows of dialysis cycles, and associate the percentage of urea and the percentage of glucose with the order of the different flows. In an embodiment, at least one drain-phase may be measured separately. In an embodiment, at least two drain-phases may be measured separately. In an embodiment, every drain-phase of a plurality of dialysis cycles may be measured separately.

Figure 3:
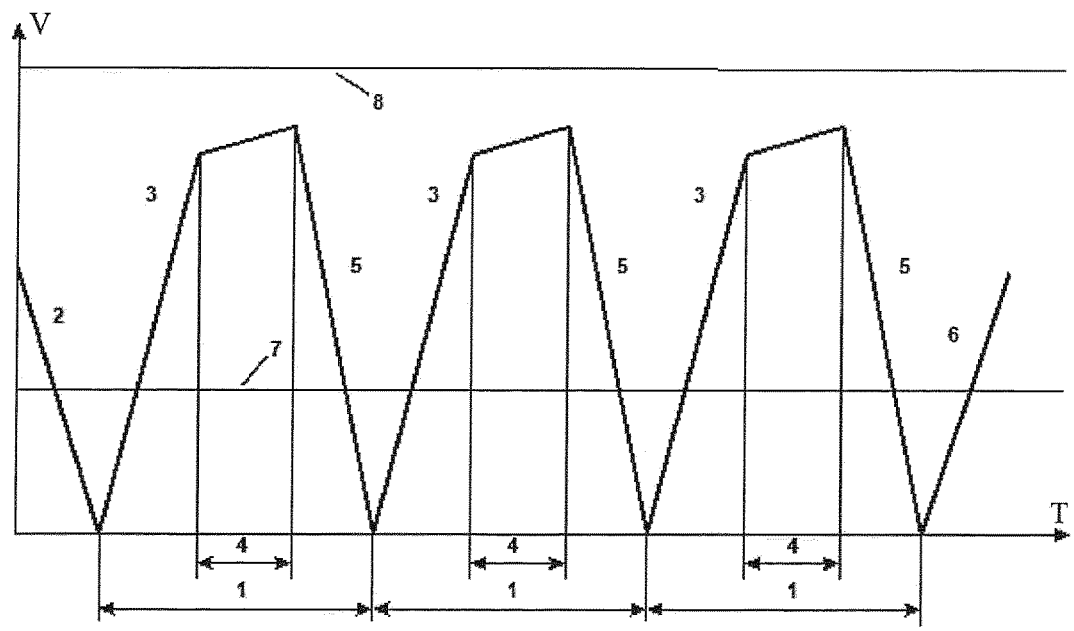
FIG. 3 illustrates an example of cycles of a peritoneal dialysis.

FIG. 3 illustrates an example of cycles of the peritoneal dialysis. The vertical axis shows a volume V in an arbitrary scale and the horizontal axis shows time T in an arbitrary scale. Continuous cycling peritoneal dialysis is a method of performing peritoneal dialysis using an automated peritoneal dialysis apparatus 10 which may perform for example 1 to 5 exchanges of dialysate every night.

Phases of a cycle of the peritoneal dialysis procedure are fill, dwell and drain. During the fill-phase, dialysate is administered through a patient tube 122 into the peritoneal cavity of a patient 12.

During a predetermined period of the dwell-phase, waste and fluid is diffused the peritoneal membrane to dialysate.

When the dwell-phase ends, spent dialysate is removed from the peritoneal cavity of the patient 12 through the drain line system 104. These phases may be repeated a plurality of times during nights.

A cycle 1 of peritoneal dialysis treatment includes a fill-phase 3 during which a peritoneal dialysis solution is instilled into the peritoneal cavity of the patient 12, a dwell-phase 4 during which dialysate gathers waste and fluid from the peritoneum, and a drain-phase 5 during which the spent dialysate with the waste and fluid is removed from the peritoneal cavity. Before starting any of the fill-, dwell- and drain-phases, a first drain-phase 2 may be performed. The first drain-phase 2 (may also be marked with 5) is similar to the drain-phase 5 after the dwell-phase 4 except that no fill-phase 3 is directly prior to it. After a final cycle, a final fill-phase 6 may be performed. The final fill-phase 6 (may also be marked with 3) is similar to the fill-phase 3 after the drain-phase 5 except that no phases of the peritoneal dialysis is performed directly after it. An allowed residual is marked using number 7 and an allowed maximum filling is marked using number 8.

In an embodiment, the data processing unit 106 may process the at least one signal for at least one of the drain-phases of the dialysis cycles. In an embodiment, the data processing unit 106 may process the at least one signal for at least two of the drain-phases of the dialysis cycles. In an embodiment, the data processing unit 106 may process the at least one signal for each of the drain-phases of the dialysis cycles. In this manner, it is possible to have detailed information on the peritoneal dialysis which be used to determine how efficient the peritoneal dialysis actually is. Additionally, it is possible to have information on successive drain-phases which may be used to increase the information on the efficiency and quality of the peritoneal dialysis.

In an embodiment, the at least one electrochemical sensor 110 may additionally continuously output at least one electric signal in response to contents of at least one of the following of the spent dialysate: protein, creatinine, at least one electrolyte and phosphate. The data processing means 106 may then form a percentage of them included in the spent dialysate based on the at least one electric signal. Creatinine indicates kidney health, for example. Creatinine comes from a biological process of creatine, phosphocreatine and adenosine triphosphate.

Figure 4:
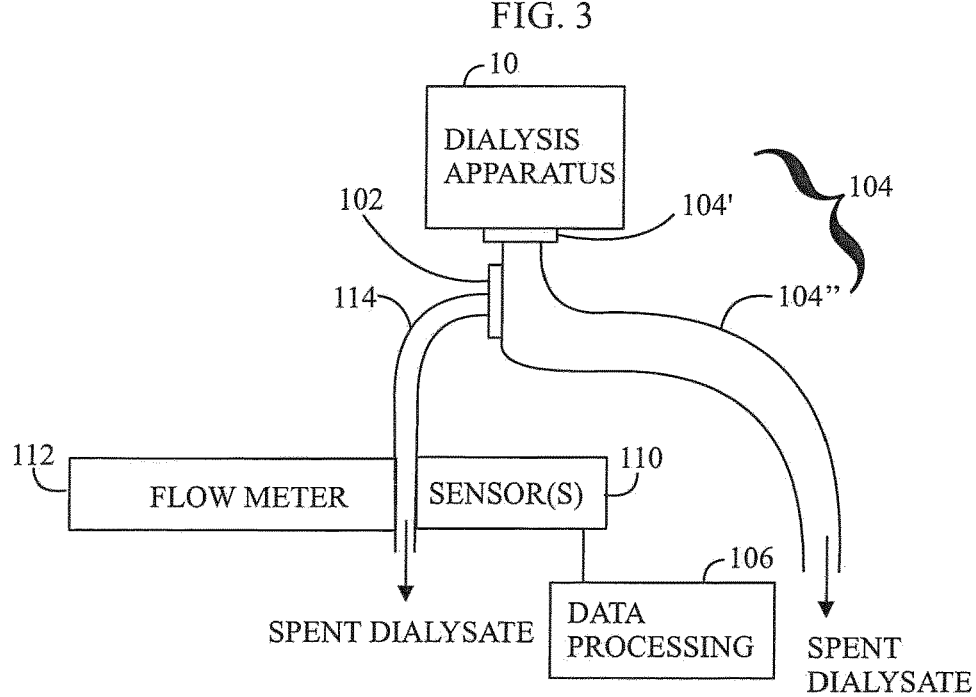
FIG. 4 illustrates an example of a measurement apparatus with a bypass line.

In an embodiment an example of which is illustrated in FIG. 4, the measurement apparatus 100 may comprises a bypass line 114, which, in turn, comprises the at least one electrochemical sensor 110. The bypass line 114 may receive a portion of the spent dialysate from the drain line system 104 of the peritoneal dialysis apparatus 10. The at least one electrochemical sensor 110 may thus be in contact with the spent dialysate of the bypass line 114.

Figure 2:
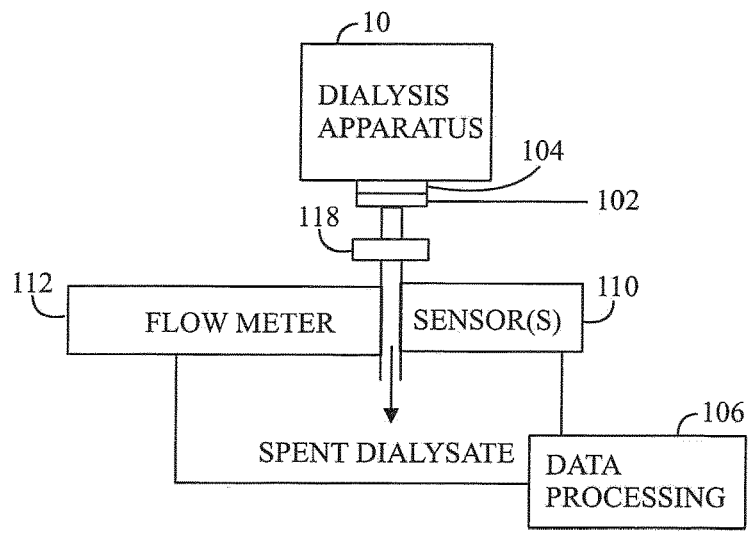
FIG. 2 illustrates an example of a measurement of spent dialysate and its flow in the drain line.

In an embodiment examples of which are illustrated in FIGS. 1, 2 and 4, the connector 102 may be contacted with at least one of the following: a drain connector 104' of the peritoneal dialysis apparatus 10 and a drain line 104". That is, the connector 102 may be in connection with the drain connector 104' and in this manner it is adjacent to the peritoneal dialysis apparatus 10. Alternatively, the connector 102 may be in connection with the drain line 104" and in this manner it may reside further from the peritoneal dialysis apparatus 10 at a desirable location along the drain line 104".

The drain connector 104' and the drain line 104" may guide the spend dialysate from the patient 12 to a sewer 116, when the spend dialysate is received through the patient line 122.

In an embodiment an example of which is illustrated in FIG. 2, the measurement apparatus 100 may comprise a filter 118, which may separate at least one of the following: fibrin and blood cells out prior to a contact with the at least one electrochemical sensor 110 in a direction to the flow of the spent dialysate. In this manner, fibrin and blood cells do not became in contact with the at least one electrochemical sensor 110 and fibrin and blood cells cannot disturb the measurement. Filtration is based on a physical operation that separates solid matter and fluid from a mixture with a porous filter medium that has a complex structure through which the fluid can pass.

In an embodiment an example which is shown in FIG. 1, the measurement apparatus 100 may perform a calibration in response to a contact between a predetermined liquid and the at least one electrochemical sensor 100. During the calibration, a predetermined liquid is flown through the drain line system 104, and the data processing unit 106 is set output predetermined values for the measured substances based on the at least one electrical signal from the at least one electrochemical sensor 100. The predetermined liquid may come from the bank 11 of solutions. The calibration may be considered as a baseline correction. In an embodiment, the predetermine liquid may include a known percentage of urea and glucose and the data processing unit 106 is set to show values which corresponds to the percentages. In an embodiment, the predetermined liquid may also include a known percentage of protein, creatinine, at least one electrolyte and phosphate, and the data processing unit 106 may be set to show values which corresponds to the percentages. Typically a standard solution is used as the predetermined liquid. The predetermined liquid may be a clean dialysate i.e. non-spent dialysate, for example.

In an embodiment, the measurement apparatus 100 may perform the calibration during every dialysis cycle, which includes dwell-phase during which the predetermined liquid is fed to the drain line system 104.

In an embodiment an example of which is illustrated in FIG. 1, the measurement apparatus 100 may comprise a clock 120. The clock 12 may be included or connected with the data processing unit 106. The measurement apparatus 100 may also comprise the flow meter 112, which may feed data on the flow of the spent dialysate that is received by the measurement apparatus 100 to the data processing 106. The data processing unit 106 may then time-stamp different flows of the dialysis cycles on a basis of a time signal from the clock 120, and associate the percentage of urea and the percentage of glucose with the time-stamps. In a corresponding manner, the data processing unit 106 may time stamp the percentages of protein and creatinine. In this manner, a detailed information as a function of time can be gathered from the spent dialysate. The information on a certain phase may be utilized for a next phase of the peritoneal dialysis. The information may also be used by a nefrologist, for example.

In an embodiment, the data processing unit 106 may form a peritoneal equilibration test (PET) value and/or a peritoneal function test (PFT) value. These values reflect how well the peritoneal cavity of the patient 12 function.

In an embodiment, an amount or contents of the dialysate may be varied on the basis of the information. In an embodiment, a period of time between the phases of the dialysis may be varied on the basis of the information.

In an embodiment, a number of dialyze phases may be varied on the basis of the information.

In an embodiment, a period of time between the dialysis may be varied on the basis of the information.

In an embodiment, a warning may be presented to the patient 12 if the values of the measurement deviate from a range that is medically acceptable. What is medically acceptable is determined in books of medicine. A person skilled in the art and medical personnel such as a doctor is familiar with acceptable values and non-acceptable values. Non-acceptable values may refer to failure of a proper operation of the dialysis process, failure in peritoneal cavity function or an illness, for example.

In an embodiment, an alarm may be raised if the values of the measurement deviate from a range that is medically acceptable. The alarm may directed to the patient 12, a close person to the patient 12, a caretaker, and/or a medical personnel. The alarm may be presented to the patient 12 as a sound and/or light. The alarm may be sent to a close person to the patient 12, the caretaker, and/or the medical personnel as telephone message. The telephone message may be sound, a text message and/or a graphic presentation on a screen of a mobile phone or a computer.

In an embodiment, the data processing unit 106 may comprise one or more processors 500 and one or more memories 502. The one or more memories 502 may include a computer program code that may process the at least one signal and information carried by the at least one signal. The one or more memories 502 and the computer program code may, with the one or more processors 500, cause the measurement apparatus 100 at least to form a percentage of urea and a percentage of glucose of the spent dialysate based on the at least one electric signal. Percentages of any other substances of the spent dialysate may also be formed in a corresponding manner. The data processing unit 106 may also control the peritoneal dialysis apparatus 10 in an automated manner.

As a conclusion it can be explained that when the patient 12 connects himself/herself with the automated peritoneal dialysis apparatus 10 he/she connects himself/herself also with the measurement apparatus 100. The measurement apparatus 100 automatically and all the time measures and stores results of the desired substances of the spent dialysate. In an embodiment as an example of FIG. 1 illustrates, the measurement apparatus 100 may comprise a transmitter 130 which may transmit, in a wired manner or a wireless manner, the results during the measurement is going on to a clinic, a hospital or the like (external computer 202 in FIG. 1), where the results may be analyzed by one or more experts. The patient 12 may visit a laboratory for a blood test once a month, for example, and the blood test analysis may be analyzed against the results of the peritoneal dialysis. The computer of the laboratory, the clinic, the hospital, the data processing unit 106, or any medical facility having a proper computer, the blood test analysis and the results of the peritoneal dialysis may compute a condition of the peritoneal membrane of the patient 12. The condition may be permeability, for example.

When more and more peritoneal cycles and blood tests are performed, a self-learning neural network or artificial intelligence may be used to resolve and predict medically significant changes of functions of the peritoneal membrane of the patient 12. The data processing unit 106, a computer of a medical facility (external computer in FIG. 1) and/or a cloud server 200 may comprise the self-learning neural network or artificial intelligence. With or without the self-learning neural network/artificial intelligence it is possible to start the peritoneal dialysis with lower volumes and lower sugar content because the measurement apparatus 100 can quickly notice underdialysis and alter the peritoneal dialysis more effective such that the peritoneal dialysis uses larger volumes and/or higher sugar content. These changes may be introduced right after one peritoneal dialysis treatment such that a next peritoneal dialysis uses the altered volumes and/or content. The changes may also be introduced even peritoneal cycle by peritoneal cycle. All these features have a positive effect on wellbeing of the patient 12.

Table 1 below illustrates examples of measuring ranges of clinical analytes in spent dialysate which are possible for the measurement apparatus.

TABLE 1

| Measuring ranges of clinical analytes in spent dialysate | |
|---|---|
| Component | Concentration |
| Anhydrous glucose | 0-240 mmol/L |
| Urea | 0-100 mmol/L |
| Creatinine | 0-1000 µmol/L |
| Total protein | 0-10 g/L |
| Phosphate | 0-5 mmol/L |

Figure 6:
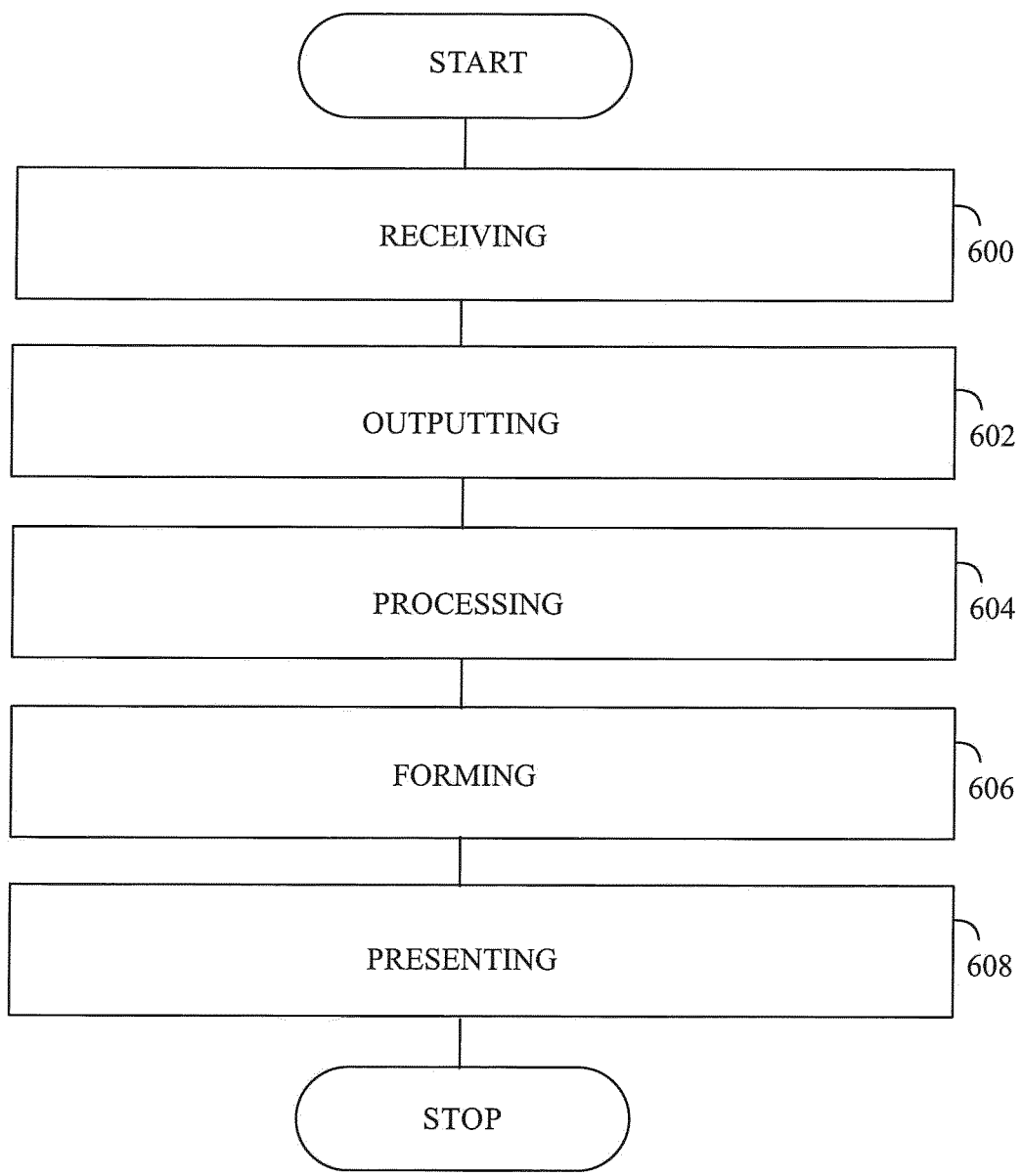
FIG. 6 illustrates of an example of a flow chart of a measuring method of a peritoneal dialysis.

FIG. 6 is a flow chart of the measurement method. In step 600, spent dialysate is received through a drain line system 104 of the peritoneal dialysis apparatus 10 by a measurement apparatus 100, when the dialysis apparatus 10 is connected with a patient 12 using a patient tube 122. In step 602, at least one electric signal is output continuously, by a at least one electrochemical sensor 110 which is in contact with a flow of the spent dialysate, in response to contents of urea and glucose of the spent dialysate. In step 604, the at least one electric signal is processed continuously by a data processing unit 106. In step 606, a percentage of urea and a percentage of glucose of the spent dialysate based on the at least one electric signal is formed continuously by the data processing unit 106. In step 608, the percentage of urea and the percentage of glucose is presented by a user interface 108.

Figure 5:
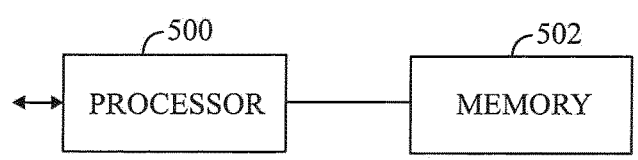
FIG. 5 illustrates an example of a data processing unit.

The method shown in FIG. 6 may be implemented as a logic circuit solution or computer program (see FIG. 5). The computer program may be placed on a computer program distribution means for the distribution thereof. The computer program distribution means is readable by the data processing unit 106 or some other suitable computer, and it encodes the computer program commands, carries out the measurements and optionally controls the automate peritoneal dialysis apparatus 10 on the basis of the measurements.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

The invention claimed is:

1. A measurement apparatus for a peritoneal dialysis apparatus, wherein the measurement apparatus comprises
    a connecting means, which is configured to be in contact with a drain line system of the peritoneal dialysis apparatus;
    at least one electrochemical sensor means;
    a clock providing a time signal;
    data processing means;
    a user interface means for the data presentation; and a flow meter, which is configured to feed data on the flow of the spent dialysate that is received by the measurement apparatus to the data processing means for detecting an order of different flows of dialysis cycles; and
    the measurement apparatus is configured to receive a predetermined liquid for calibration during every dialysis cycle, which includes dwell-phase during which the predetermined liquid is fed to the drain line system, and spent dialysate through the drain line system of the peritoneal dialysis apparatus, the spent dialysate being received when the dialysis apparatus is connected with a patient;

the at least one electrochemical sensor means, which is configured to be in contact with the predetermined liquid for the calibration and the spent dialysate, is configured to continuously output at least one electric signal in response to contents of urea and glucose of the predetermined liquid for the calibration and the spent dialysate for data processing and/or data presentation of the at least one electric signal; and the data processing means is configured to receive data on the flow of the spent dialysate;

continuously process the at least one electric signal, form a percentage of urea and a percentage of glucose of the spent dialysate based on the at least one electric signal, time-stamp different flows of dialysis cycles on a basis of the time signal from the clock, associate the percentage of urea and the percentage of glucose with the time-stamps; and the user interface is configured to present the percentage of urea and the percentage of glucose associated with the time-stamps.

2. The measurement apparatus of claim 1, wherein the measurement apparatus comprises the flow meter which is configured to feed data on flow of the spent dialysate that is received by the measurement apparatus to the data processing and/or the data presentation for detecting an order of different flows of dialysis cycles, and associating the data processing and/or the data presentation with percentage of urea and the percentage of glucose with the order of the different flows.

3. The measurement apparatus of claim 2, wherein the at least one electrochemical sensor means is configured to output the at least one electric signal for data processing the at least one signal for each of the dialysis cycles.

4. The measurement apparatus of claim 1, wherein the at least one electrochemical sensor means is additionally configured to continuously output, for forming a percentage of contents included in the spent dialysate based on the at least one electric signal, at least one electric signal in response to the contents of at least one of the following of the spent dialysate: protein, creatinine, at least one electrolyte and phosphate.

5. The measurement apparatus of claim 1, wherein the measurement apparatus comprises a bypass line, which comprises the at least one electrochemical sensor means, and is configured to receive a portion of the spent dialysate from the drain line system of the peritoneal dialysis apparatus; and the at least one electrochemical sensor means is configured to be in contact with the spent dialysate of the bypass line.

6. The measurement apparatus of claim 1, wherein the connecting means is configured be contacted with at least one of the following: a drain connector of the peritoneal dialysis apparatus and a drain line, the drain connector and the drain line being configured to guide the spend dialysate from the patient to a sewer.

7. The measurement apparatus of claim 1, wherein the measurement apparatus comprises filtering means, which is configured to separate at least one of the following: fibrin and blood cells out prior to a contact with the at least one electrochemical sensor means.

8. The measurement apparatus of claim 1, wherein the data processing means is configured to detect an order of different flows of dialysis cycles, and associate the percentage of urea and the percentage of glucose with the order of the different flows.

9. An automated peritoneal dialysis apparatus, wherein the automated peritoneal dialysis apparatus comprises the measurement apparatus of claim 1.

10. The automated peritoneal dialysis apparatus of claim 9, wherein the measurement apparatus comprises a flow meter, which is configured to feed data on the flow of the spent dialysate that is received by the measurement apparatus to the data processing means.

11. A measuring method of a peritoneal dialysis apparatus, the method comprising receiving, by a measurement apparatus, a predetermined liquid for calibration during every dialysis cycle, which includes dwell-phase during which the predetermined liquid is fed to a drain line system and spent dialysate through the drain line system of the peritoneal dialysis apparatus, the spent dialysate being received when the dialysis apparatus is connected with a patient using a patient tube for detecting an order of different flows of dialysis cycles;

outputting continuously, by at least one electrochemical sensor means, which is in contact with the predetermined liquid for the calibration and a flow of the spent dialysate, at least one electric signal in response to contents of urea and glucose of the predetermined liquid for the calibration and the spent dialysate;

processing continuously, by a data processing means, the at least one electric signal;

forming continuously, by the data processing means, a percentage of urea and a percentage of glucose of the spent dialysate based on the at least one electric signal;

time-stamping different flows of dialysis cycles on a basis of the time signal from a clock;

associating the percentage of urea and the percentage of glucose with the time-stamps; and presenting, by a user interface, the percentage of urea and the percentage of glucose associated with the time-stamps.

* * * * *